(12) United States Patent
Tang et al.

(10) Patent No.: US 10,889,540 B2
(45) Date of Patent: Jan. 12, 2021

(54) PREPARATION METHOD OF A FORMAMIDE COMPOUND

(71) Applicant: BEIJING J-TEC TECHNOLOGY CO., LTD., Beijing (CN)

(72) Inventors: Chenghan Tang, Beijing (CN); Yunjian Zhao, Beijing (CN); Anxing Wei, Beijing (CN); Wei Guo, Beijing (CN)

(73) Assignee: BEIJING J-TEC TECHNOLOGY CO., LTD, Beijing (CN)

( * ) Notice: Subject to any disclaimer, the term of this patent is extended or adjusted under 35 U.S.C. 154(b) by 0 days.

(21) Appl. No.: 15/871,856

(22) Filed: Jan. 15, 2018

(65) Prior Publication Data

US 2019/0071391 A1    Mar. 7, 2019

(30) Foreign Application Priority Data

Sep. 4, 2017   (CN) .......................... 2017 1 0785720

(51) Int. Cl.
| | | |
|---|---|---|
| *C07C 221/00* | (2006.01) | |
| *C07C 231/02* | (2006.01) | |
| *C07D 207/06* | (2006.01) | |
| *C07D 295/108* | (2006.01) | |

(52) U.S. Cl.
CPC .......... *C07C 221/00* (2013.01); *C07C 231/02* (2013.01); *C07D 207/06* (2013.01); *C07D 295/108* (2013.01); *C07C 2601/14* (2017.05)

(58) Field of Classification Search
None
See application file for complete search history.

(56) References Cited

U.S. PATENT DOCUMENTS

2011/0137081 A1* 6/2011 Krull ..................... B01J 19/126
564/139

FOREIGN PATENT DOCUMENTS

| CN | 102712576 A | 10/2012 |
|---|---|---|
| CN | 104447379 A | 3/2015 |
| CN | 106278923 A | 1/2017 |
| CN | 107056567 A | 8/2017 |

OTHER PUBLICATIONS

The Chinese First Examination Report of corresponding Chinese application No. 201710785720.7, dated Mar. 20, 2019.
Yun, Kuihong, "Aliphatic Carboxylic Acids and Derivatives" College Textbook published by Higher Education Press; (Apr. 1955); pp. 15.
The Chinese Second Examination Report of corresponding Chinese application No. 201710785720.7, dated Aug. 26, 2019.
Research Letter, Green Chemistry Letters and Reviews, vol. 4, No. 2, Jun. 2011 (151-157).
Third Office Action of the prior Chinese application, dated Mar. 12, 2020.

* cited by examiner

*Primary Examiner* — Sudhakar Katakam
*Assistant Examiner* — Jennifer C Sawyer
(74) *Attorney, Agent, or Firm* — J.C. Patents (57) ABSTRACT

The present application provides a preparation method of a formamide compound, the preparation process includes: uniformly mixing raw material of methanoic acid and an amine compound selected from a primary amine or a secondary amine to prepare a homogeneous reaction system; the above homogeneous reaction system is heated to 160-230° C., allowing carbon monoxide to be decomposed from the homogeneous reaction system and participates in the reaction, and collecting the reaction product to obtain a formamide compound. The present application provides a new technology using a homogeneous method to synthesize a formamide compound, the reaction process needs no use of a catalyst, the operation process is simple and controllable, and the raw material of the amine compound has a high selectivity.

19 Claims, 4 Drawing Sheets

PREPARATION METHOD OF A FORMAMIDE COMPOUND

CROSS-REFERENCE TO RELATED APPLICATION

This application claims priority to Chinese Patent Application No. 201710785720.7, filed on Sep. 4, 2017, which is hereby incorporated by reference in its entirety.

TECHNICAL FIELD

The present application relates to a preparation method of a formamide compound, belonging to the field of chemical synthesis technology.

BACKGROUND

Formamide compound is a product of carbonylation synthesis of a primary amine compound or a secondary amine compound, i.e., a compound generated after a carbonyl (—CO) is introduced between a nitrogen atom and a hydrogen atom of the primary amine or the secondary amine compound. The formamide compound is an important chemical raw material, which generally serves as a solvent, an extractant and an intermediate in organic synthesis, such as pharmaceutical synthesis.

Currently, there are many methods for the preparation of formamide compound, among which representative ones are mainly formic ether method and carbonylation method, for example, patent application CN102712576A discloses a method for synthesizing an aromatic formamide by catalyzing the reaction between an aromatic amine and a formic ether (such as methyl formate, ethyl formate, propyl formate, etc.) with a $C_1$-$C_4$ alkyl phosphonic acid or a Lewis acid metal salt as a catalyst, wherein the raw material of formic ether is required to be excessive due to low efficiency of the reaction (molar ratio of the reactant is up to 5:1). And the patent application CN106278923A discloses that, carbon monoxide is introduced for performing a carbonylation reaction, with hydroxyl tridymite SiQ carried noble metal ruthenium as a catalyst, methanol as a solvent, a primary amine or a secondary amine compound as a raw material, so as to obtain a formamide compound.

Numerous preparation methods of formamide compound have already been proposed, yet with certain disadvantages, for example, when using the formic ether method, there are not only the problem in the separation and purification of the product caused by the catalyst, but also the problem of corrosion of reaction equipments caused by the catalyst. Whereas in the carbonylation method requiring introduction of carbon monoxide, the preparation process of the used catalyst of noble metals is complex and the cost is high, while the catalyst also brings about certain challenges to separation and purification of the subsequent product; in addition, the carbonylation system introducing carbon monoxide is a heterogeneous reaction system, which is required to undergo the carbonylation under a stringent technical conditions for increasing the solubility of carbon monoxide, and hence is bad for practical industrial production.

Overall, although there is an obvious demand for formamide compounds in chemical product production, currently, either the formic ether method or the carbonylation method more than often adopts a heterogeneous reaction system, both with high demand for preparation technology control, manufacturing enterprises invest heavily but it is difficult to satisfy scale requirements; and in order to improve the selectivity and yield of a target product, selection and use of a catalyst is of vital importance, and there shall be corresponding technology and operation requirements for synthetic technology and regeneration of the catalyst. The noble metal catalyst itself, regeneration technology thereof and the limited service life (for example, in patent application CN106278923A, that the catalyst can be recycled for more than 4 times has been deemed as one of the beneficial effects of the technology), inevitably increases the production cost, and high requirements by a catalyst-containing reaction system for separation and purification technology of a formamide target product is also an important factor in curtailing production scale of the formamide product. In spite of ever-lasting study on the production technology of formamide products, the use of metal catalysts and the heterogeneous reaction system are involved throughout. And numerous factors result in limitation on production efficiency of the formamide compound, and the product cost remains high.

Therefore, it is critically important to develop a new technology of homogeneous method for synthesizing a formamide compound, which is simple and needs no use of a catalyst in the synthetic process, for improving the level of industrial production of the formamide compound and lowering the usage cost of formamide products.

SUMMARY

Directed against the drawbacks in the prior art, the present application provides a preparation method of a formamide compound, which is performed in a homogeneous reaction system, without using a catalyst, has high selectivity, and is conducive to industrial production and practical applications.

The present application provides a preparation method of a formamide compound, preparation process includes:

mixing raw materials, i.e., methanoic acid and an amine compound selected from a primary amine or a secondary amine, to prepare a homogeneous reaction system;

heating the above homogeneous reaction system to 160-230° C., to allow carbon monoxide to be decomposed from the homogeneous reaction system and to take part in reaction, and collecting reaction product to obtain the formamide compound.

The inventor finds after studies that, a homogeneous reaction system can be obtained by merely mixing raw materials of methanoic acid and a primary amine compound or a secondary amine compound, and further carbon monoxide can be decomposed from the homogeneous reaction system by appropriate control of reaction conditions such as the reaction temperature and without using a catalyst, the carbon monoxide has high activity and can take part in reaction in the homogeneous system (i.e., can realize carbonylation reaction), a formamide compound is generated and water is released. It is based on the above research and findings that the present invention is accomplished.

According to the method and result of the present application, a homogeneous reaction is occurred when methanoic acid and a primary amine compound or a secondary amine compound are taken as raw materials and mixed, the obtained homogeneous reaction system is an ionic liquid product of a methanoic acid-secondary amine salt (a homogeneous liquid system), when the ionic liquid is subjected to a certain temperature, highly active CO will be decomposed out and immediately a carbonylation reaction is happened, so that a predetermined formamide target product is obtained while water is released, which is represented by the following chemical reaction formula:

Due to the entire preparation process of the formamide compound being performed in a homogeneous system without requiring a catalyst, the obtained reaction product only requires undergoing conventional separation and refining to obtain a final product satisfying the demand for application, and the reaction product can even be directly used as a final product after flash dewatering, resulting in high controllability of the technology.

According to embodiments of the present application, methanoic acid is mixed with a primary amine or secondary amine compound to obtain a homogeneous reaction system, which is heated to about 160° C. or higher for initiating a reaction, during which decomposition is performed to generate CO while pressure in the system increases, the highly active CO enters the homogeneous system followed by immediate occurrence of a carbonylation reaction, generating a formamide product. Therefore, completion of the reaction can be determined by tracking and monitoring the reaction process and the generation of CO gas during the reaction process. In an actual industrial production process, the above preparation technique is usually completed in a conventional high-pressure reactor (such as a reactor made of a titanium molybdenum nickel material) which resists corrosion by methanoic acid. Because the generation and existence of CO brings pressure change in the high-pressure reactor, so the end point of the reaction can be determined by monitoring the pressure in the high-pressure reactor to be stabilized for a certain reaction time instead of increasing.

During the heating process of the above homogeneous reaction system composed of the ionic liquid, pressure in the high-pressure reactor increases accordingly. Taking all into consideration, the homogeneous reaction system is heated to 160° C.-230° C. under control, allowing the pressure in the system to reach 1.0 Mpa-3.0 Mpa and no higher (normally, the pressure is observed to be stabilized at a certain value instead of increasing), the condition is kept for a certain reaction time, which may usually be 1-5 hours (for example, 2-5 hours, or 2-4 hours), substantially allowing no more generation of carbon monoxide. And the generated carbon monoxide is consumed in the reaction, which is to say, the reaction in the homogeneous reaction system is also complete, and unreacted methanoic acid has also been entirely decomposed into carbon monoxide and water, based on which it can be judged that the reaction is complete.

As mentioned above, the preparation method of the present application is performed in a homogeneous reaction system, and the finally generated formamide compound also exists in the form of a solution. Preservation of a modest amount of solvent in the homogeneous reaction system also facilitates maintaining a stable homogeneous system and product treatment. An acceptable solvent normally shall satisfy both or either of the following conditions:

1) the solvent is able to be homogeneously miscible with the above homogeneous reaction system;

2) the solvent is able to be miscible with a formamide compound target product.

According to embodiments of the present application, the prepared homogeneous reaction system contains a solvent which is water, or a solvent miscible with water, or a solvent immiscible with water but miscible with the generated formamide target product. Water is released during the reaction process, and the selected raw material of methanoic acid, restricted by purity, usually also introduces a certain amount of water, as a result, water from both sources are finally present in the homogeneous reaction system of the present application. And a modest amount of water or other solvent may also be additionally added if needed. In other words, the above solvent may be water, or a water dissolved organic matter (Dissolved Organic Matter, DOM) miscible with water, such as methanol, ethanol, islpropanol and the like; the selected solvent may also be immiscible with water but miscible with a formamide compound, for example, may be well miscible with a formamide compound containing a heterocyclic ring or an aromatic ring, and again, for example, may be well miscible with a formamide compound containing more than 2 long carbon chains (such as an chain alkane with more than 2 carbon chains containing more than 6 carbon atoms ($C_6$) in the molecule). In a specific embodiment, the solvent may be water formed during the process for preparing the homogeneous reaction system from methanoic acid and the amine compound, and/or water added during the process for preparing the homogeneous reaction system from methanoic acid and the amine compound, and/or one or more of organic solvents of dioxane, tetrahydrofuran, methanol, ethanol, isopropanol, dimethylformamide, toluene and xylene.

Too much solvent is unfavorable, whereas there is no restriction to the amount of the solvent. Usually, the required amount of the solvent just allows the formamide compound in the reaction product to reach a saturated solubility or a little more than that. For example, the amount is roughly 1.0-1.2 times that is required for the formamide compound in the reaction product to reach its saturated solubility. With the amount of the solvent increasing, conversion rate of the primary amine or the secondary amine compound experiences a minor decline, which does not undermine the selectivity, but is likely to increase workload for subsequent purifying and refining, and unreacted raw material of amine compound may be recycled after separation.

Commercially available raw material of methanoic acid usually contains a certain amount of water. For example, methanoic acid, as a chemical raw material, usually has a purity of 85%, besides which, methanoic acid with a purity of 98% can also be purchased or prepared by oneself. Therefore, during practical production, water contained in the raw material of methanoic acid is introduced to the reaction system more or less to act as a solvent, and water is continuously generated in the reaction process which also acts as part of the solvent. Therefore, when the selected raw material of methanoic acid contains a high amount of water, there is generally no need to add additional solvent water or other solvent during the production operation process.

For the purpose of clarity, solvent water additionally added during the production operation process of the present application is referred to as "external water", so as to distinguish water in the raw material of methanoic acid and water released in the reaction process. In description, the total amount of the solvent water added into the reaction system should be construed as the sum of the water contained in methanoic acid plus the external water.

It is understandable that, reasonably controlling the ratio of the reaction raw materials is conducive to improving the conversion rate of the raw materials and reducing production cost entailed by separation and recycling of the raw materials. According to the preparation method of the present application, the primary amine or secondary amine compound is converted into the formamide product with a very high selectivity and few by-reactions, therefore, the amount of substance of methanoic acid and the primary amine or the secondary amine compound are usually controlled to be or basically be equivalent based on stoichiometric coefficient of reaction, allowing subsequent process to be simple. If the raw material of methanoic acid is excessive, surplus methanoic acid will be decomposed into carbon monoxide, exerting no influence on subsequent refining of the reaction product; if the raw material of the primary amine or the secondary amine compound is excessive, incompletely reacted primary amine or secondary amine compound will remain in the reaction system, which can be recycled and reused as a raw material by purifying and refining the reaction product.

In a practical industrial production process, out of consideration of the conversion rate of raw materials, refining of the subsequent product as well as operation cost and other factors, the raw material of methanoic acid is usually controlled to be slightly excessive, for example, the molar ratio of methanoic acid to the primary amine or the secondary amine compound is (1.02-1.3): 1, and is further (1.02-1.1):1, so as to obtain a high product yield while facilitating purification and refining of the product.

As stated above, the whole preparation process of the present application does not introduce catalysts and the like, the reaction process is simple, and with very few by-reactions. The reaction product, after surplus carbon monoxide and water steam being removed therefrom and possible incompletely reacted primary amine or secondary amine compound therein being recycled, can directly act as an applicable product. Even if factors such as the purity of the raw material impacts yield and purity of the product, subsequently the reaction product is only required to be subjected to purification and refining via conventional means in this field, such as via flash dewatering and/or vacuum rectification, to realize purification of the reaction product.

In the present application, there is no restriction on the purity (i.e., purity and the amount of water) of the raw material of methanoic acid, and if it is considered to be necessary, appropriate refining and purification may also be carried out in the first place, which is conducive to simplifying the subsequent refining process. Typically, all primary amine compounds or secondary amine compounds used in a carbonylation synthesis process for preparing a formamide compound can serve as a raw material in the present application.

In embodiments of the present application, the used amine compound of a primary amine or a secondary amine has a molecular formula $R_1R_2NH$, wherein: each of $R_1$ and $R_2$ groups is independently selected from hydrogen but not both hydrogen, $C_1$-$C_{14}$ hydrocarbyl, and $C_1$-$C_{14}$ hydrocarbyl containing 1-2 substituent groups; or, the primary amine or the secondary amine compound is a five-membered nitrogen-containing heterocyclic ring or six-membered nitrogen-containing heterocyclic ring compound with a molecule having at least one active hydrogen, and the five-membered nitrogen-containing heterocyclic ring or six-membered nitrogen-containing heterocyclic ring does not contain substituent group or contains 1-2 substituent groups;

The above 1-2 substituent groups are selected from halogen, such as —F, —Cl, —Br; nitro group (—$NO_2$), cyano group (—CN), lower alkoxy group, and are generally alkoxy group having 1-6 carbon atoms, such as methoxyl (—$OCH_3$), ethoxy (—$OC_2H_5$) or propoxy (—$OC_3H_7$), etc., hydroxyl group (—OH) or secondary amino group of a lower alkyl, such as —$N(CH_3)_2$, —$N(C_2H_5)_2$, —$N(CH_3)(C_2H_5)$ etc., the described lower alkyl is generally an alkyl with 1-6 carbon atoms.

The aforementioned five-membered nitrogen-containing heterocyclic ring or six-membered nitrogen-containing heterocyclic ring compound with a molecule containing at least one "active hydrogen" can be construed as, when the nitrogen-containing heterocyclic ring is formed, there should be at least one hydrogen which is liable to disassociate from the nitrogen atom under reaction conditions, according to basic chemical knowledge.

In a specific embodiment, the amine compound of a primary amine or a secondary amine has a molecular formula $R_1R_2NH$, wherein: $R_1$ is hydrogen, a $C_1$-$C_{14}$ hydrocarbyl, a $C_1$-$C_{14}$ hydrocarbyl containing 1-2 substituent groups; and R2 is a C2-C14 hydrocarbyl, and a C2-C14 hydrocarbyl containing 1-2 substituent groups; or, the primary amine or the secondary amine compound is a five-membered nitrogen-containing heterocyclic ring or six-membered nitrogen-containing heterocyclic ring compound having a pyrrole, a pyrrolidine, an imidazole, a morpholine or a piperazinyl and the like.

According to solutions of the present application, the hydrocarbyl may be selected from alkane group, cycloalkyl group or aryl group, for example $C_1$-$C_{14}$ chain alkyl, $C_3$-$C_{14}$ cycloalkyl, $C_6$-$C_{14}$ aryl. The $C_1$-$C_{14}$ chain alkyl may be $C_1$-$C_{14}$ straight chain alkyl and $C_1$-$C_{14}$ branched alkyl, for example methyl, ethyl, n-propyl, isopropyl, n-octyl, n-dodecyl, etc.; the $C_3$-$C_{14}$ cycloalkyl, for example, may be substituted or unsubstituted cyclohexyl, cyclopentane and the like, the $C_6$-$C_{14}$ aryl, for example, may be phenyl, alkyl phenyl and the like.

It should be understood that, R1 and R2 indicated in the present application merely represent two substituent groups which may exist in the molecular formula of the amine compound as a raw material, and are merely meant for facilitating description, rather than specifying position and orders of the two groups, which is to say, R1, R2 in the molecular formula may be interchanged.

According to the preparation method of the present application, because the preparation of the formamide compound is performed in a homogeneous reaction system, the overall production process is simpler compared with a conventional technology, and has fewer by-reactions, the material has a high selectivity, and the difficulty in purifying and refining the product is reduced; at the same time, there being no necessity to use a catalyst in the reaction process saves the raw material of the catalyst while reducing regeneration cost and the difficulty in separating and purifying the product. Implementation of the present application significantly reduces the difficulty in processing the formamide compound and lowers the production cost. And when the secondary amine compound or the raw material of the secondary amine compound is selected from diethylamine, dipropylamine, diisopropylamine, dibutylamine, diisobutylamine or n-butylamine, etc., the preparation method of the present application has more practical industrialization application prospect and value.

As stated above, the reaction product obtained by the method of the present application may be further purified and refined as needed, thereby providing products with a higher grade.

In summary, the present application provides a preparation method of a formamide compound, which adopts a primary amine or a secondary amine compound and methanoic acid as raw materials to undergo a homogeneous reaction, from which a formamide compound is obtained. The reaction process requires no uses of a catalyst, therefore, avoids corrosion of equipment caused by addition of the catalyst in traditional preparation technology, and avoids other relevant problems such as high cost, while reducing the difficulty in purifying the product. According to the demand for using a target product, upon simple flash dewatering and purifying treatment, a formamide compound product with a purity of higher than 99% is obtained, satisfying the demand for using the product. And no catalyst is used, eliminating the need to arrange a catalyst regeneration system and procedure, while reducing the production cost.

In the meanwhile, the above preparation method is carried out under simple reaction conditions, with a short reaction path and few by-reactions, and a high selectivity and conversion rate of the primary amine or the secondary amine compound. With the formamide product being prepared according to the solution of the present application, the raw material of the amine compound reaches a selectivity of higher than 90%, even higher than 99%, and normally, the conversion rate is able to reach higher than 80%, or even higher than 90%, facilitating industrial production and practical application of the formamide compound.

DESCRIPTION OF EMBODIMENTS

In order that the purpose, technical solutions and advantages of the present application are made clearer, elaborate descriptions will be presented as follows through specific embodiments. It should be understood that the embodiments described herein are merely part of the embodiments of the present application, and the scopes of application and protection of the present application shall be subject to contents of the claims. Based on the entire description as well as all of the embodiments, all the other embodiments obtained by one with ordinary skill in the art without delivering creative efforts shall fall into the protection scope of the present application.

Unless otherwise noted, qualitative and quantitative analysis of the reaction product and purified and refined product in the following embodiments and experimental examples adopt gas chromatographic analysis. The adopted gas chromatographic instrument, with a model number of GC2002 type (N/DF-2), is produced by Shanghai Kechuang Instruments Technology Co., Ltd, and uses a capillary chromatographic column (purchased from Lanzhou ATECH Technologies Co., Ltd, having a 60 m chromatographic column with an inner diameter of 0.32 mm, a 30 m chromatographic column with an inner diameter of 0.53 mm, a film with a thickness of 0.5 μm, and an immobile liquid of AE.PEG-20M), as well as a hydrogen flame detector.

Embodiment 1: Preparation of N,N-Diethyl Formamide 306.9 g of methanoic acid with a purity of 85% (i.e., containing water 46.04 g) is added into a high-pressure reactor with a volume of 1 litre, a stirrer is started and 395 g of diethylamine with a purity of 99% is added via a constant-flux pump into the high-pressure reactor, and the mixture is stirred uniformly, so as to obtain a homogeneous reaction system, wherein molar ratio of methanoic acid to diethylamine is 1.05:1.

With stirring continuing, the above homogeneous reaction system is heated to 160° C. and kept at the temperature for about 45 minutes, and is then heated to about 190° C. During the process, the pressure in the high-pressure reactor rises to about 1.2 MPa and substantially no higher, the reaction is maintained for about 2.5 hours, then carbon monoxide and steam in the high-pressure reactor are vented, and the reaction product is collected, so as to obtain about 700 g of a homogeneous transparent solution.

Figure 1:
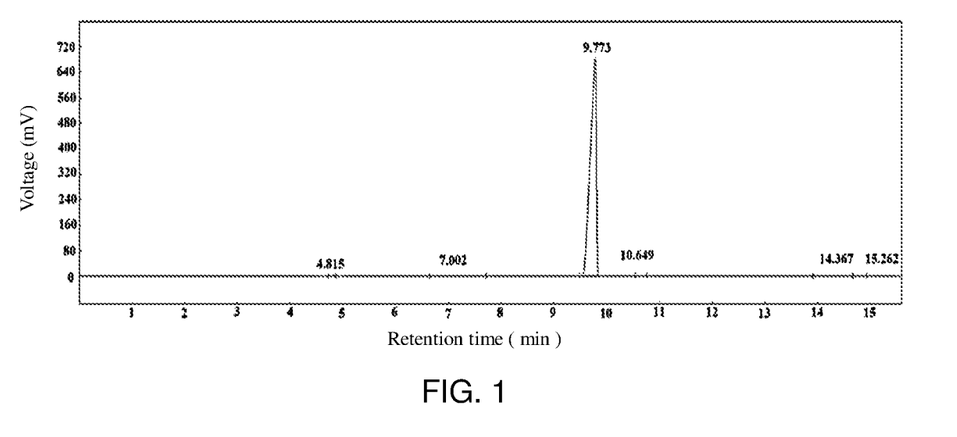
FIG. 1 is a chromatogram for reaction product in embodiment 1.

Gas chromatographic analysis result of the above reaction product is shown in the following Table 1, and the obtained chromatogram is referred to FIG. 1 (using a gas chromatography column with a length of 60 meters, under the following specific test conditions: pressure before the column: 0.1 MPa, air pressure: 0.03 MPa, pressure of hydrogen gas: 0.025 MPa, temperature in the column box: 155° C., evaporation temperature: 220° C., test temperature: 220° C., measuring range: 9, sample injection fashion: split injection, split flow rate: 21.7 mL/min, and sample injection volume: 1 μL). It can be seen from FIG. 1 and Table 1 that, two chromatographic peaks in good sharp shape and symmetrical with each other are present, and other apparent chromatographic peaks (no peaking for water) are absent under observation. Upon comparison with retention time of a standard sample, it can be determined that, the above two chromatographic peaks are characteristic peaks corresponding to diethylamine and N,N-diethyl formamide, respectively.

Since there is no peaking for water during the test process, in the analysis result, concentration of N,N-diethyl formamide can be obtained as about 99.62%, concentration of diethylamine about 0.11%. And results in the following embodiments are processed in the same manner.

Upon calculation, in this embodiment, conversion rate of diethylamine is up to more than 99%, and its selectivity is up to 99%.

The above reaction product is subjected to purifying and refining, the product contains an extremely small amount of unreacted diethylamine, the boiling point of which is significantly different from that of N,N-diethyl formamide, thus diethylamine and water in the product can be removed by performing flash dewatering and vacuum rectification to the reaction product.

Figure 2:
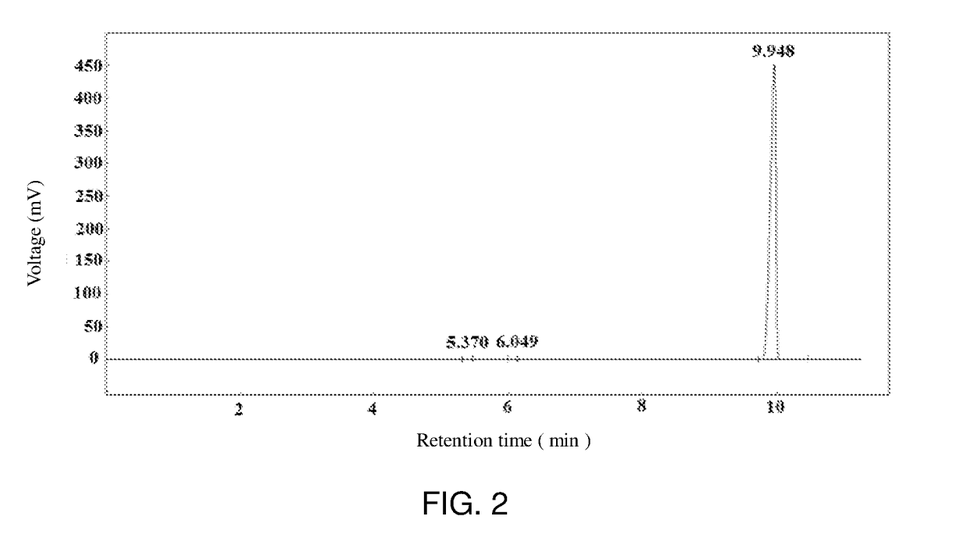
FIG. 2 is a chromatogram for the final product after purification and refining of the reaction product in embodiment 1.

Gas chromatographic analysis result of the above purified and refined product is shown in Table 2, with a chromatogram shown as FIG. 2, and the product index of refraction $N_D$ (20) is measured to be 1.4340, which further determines that the purified and refined product is N,N-diethyl formamide with a purity of about 99.96%, reaching a reagent grade.

TABLE 1

| Number | Retention time (minute) | Name | Concentration (%) | Chromatographic peak area |
|---|---|---|---|---|
| 1 | 4.815 | Diethylamine | 0.1135 | 5898 |
| 2 | 7.002 | | 0.04592 | 2387 |
| 3 | 9.773 | N,N-diethyl formamide | 99.62 | 5178222 |
| 4 | 10.649 | | 0.002921 | 152 |
| 5 | 14.367 | | 0.01099 | 571 |
| 6 | 15.262 | | 0.06473 | 3365 |
| 7 | 28.118 | | 0.01368 | 711 |
| 8 | 43.818 | | 0.02083 | 1083 |
| 9 | 59.698 | | 0.1107 | 5757 |
| Sum | | | 100 | 5198146 |

TABLE 2

| Number | Retention time (minute) | Name | Concentration (%) | Chromatographic peak area |
|---|---|---|---|---|
| 1 | 5.370 | | 0.0363 | 874 |
| 2 | 6.049 | | 0.005868 | 141 |
| 3 | 9.948 | N,N-diethyl formamide | 99.96 | 2405613 |
| Sum | | | 100 | 2406628 |

Embodiment 2: Preparation of N,N-Diethyl Formamide 94.5 g of methanoic acid with a purity of 60% (i.e., containing water 38.6 g) is added into a high-pressure reactor of 1 litre, a stirrer is started and 146.3 g of diethylamine with a purity of 99% is added via a constant-flux pump into the high-pressure reactor, and the mixture is stirred uniformly, so as to obtain a homogeneous reaction system, wherein molar ratio of methanoic acid to diethylamine is 1.05:1.

With stirring continuing, the above homogeneous reaction system is heated to 160° C. at a heating rate of about CC/minute, and kept at the temperature for about 45 minutes, and is then heated to about 190° C., and the reaction is maintained for about 2.5 hours. During the process, the pressure in the high-pressure reactor rises to about 1.3 MPa and no higher and is substantially stable. Then carbon monoxide and steam in the high-pressure reactor are vented, and the reaction product is collected, so as to obtain about 235 g of a homogeneous transparent solution.

Upon chromatographic analysis and comparison of the above reaction product, it is determined that N,N-diethyl formamide with a concentration of about 90.3% is synthesized, and the reaction product contains incompletely reacted diethylamine with a concentration of about 9.64%. Upon calculation, the conversion rate of diethylamine is up to more than 90%, and the generated N,N-diethyl formamide has a selectivity of 99%.

Flash dewatering and vacuum rectification technology are adopted to perform purification and refining to the above reaction product, so as to recycle the incompletely reacted diethylamine and remove the water therein, thereby obtaining N,N-diethyl formamide product with a purity of greater than 99.9%, which reaches a reagent grade.

Embodiment 3: Preparation of N,N-Dipropyl Formamide 284.1 g of methanoic acid with a purity of 85% (i.e., containing water 42.6 g) is added into a high-pressure reactor with a volume of 1 litre, a stirrer is started and 506 g of dipropylamine with a purity of 99% is added via a constant-flux pump into the high-pressure reactor, and the mixture is stirred uniformly, so as to obtain a homogeneous reaction system, wherein molar ratio of methanoic acid to dipropylamine is 1.06:1.

With stirring continuing, the above homogeneous reaction system is heated to 160° C. and kept at the temperature for about 50 minutes, and is then heated to about 190° C. The pressure in the high-pressure reactor rises to about 1.2 MPa and no higher and is substantially stable, the reaction is maintained for about 2.5 hours, then carbon monoxide and steam in the high-pressure reactor are vented, and the reaction product is collected, so as to obtain about 780 g of a homogeneous transparent solution.

Upon chromatographic analysis and comparison of the above reaction product, N,N-dipropyl formamide with a concentration of about 98.82% is determined to be obtained, the product also contains a small amount of dipropylamine with a concentration of about 1.17%. Upon calculation, the conversion rate of dipropylamine is up to more than 98%, and its selectivity is 99%.

Flash dewatering and vacuum rectification are performed to the above reaction product, and the purified and refined product is subjected to chromatographic analysis, the concentration of which is measured to be about 99.93%, and the index of refraction $N_D$ (20) of which is measured to be 1.4398, suggesting that after purification and refining, N,N-dipropyl formamide with a purity of higher than 99.9% is obtained, which is higher than a reagent grade.

Embodiment 4: Preparation of N,N-Dibutyl Formamide 170.5 g of methanoic acid with a purity of 85% (i.e., containing water 25.5 g) and 391 g of dibutylamine with a purity of 99% are added into a high-pressure reactor with a volume of 1 litre, a stirrer is started, and the stirring is performed to achieve a homogeneous effect, so as to obtain a homogeneous reaction system, wherein molar ratio of methanoic acid to dibutylamine is 1.05:1.

With stirring continuing, the above homogeneous reaction system is heated to 160° C. and kept at the temperature for about 55 minutes, and is then heated to about 190° C. The pressure in the high-pressure reactor rises to about 1.2 MPa and no higher and is substantially stable, the reaction is maintained for about 2.5 hours, then carbon monoxide and steam in the high-pressure reactor are vented, and the reaction product is collected, so as to obtain about 557 g of a homogeneous transparent solution.

The above reaction product is subjected to chromatographic analysis, and the obtained chromatographic analysis result is compared with that of a standard sample, so as to determine that N,N-dibutyl formamide with a concentration of about 98.19% is obtained, the product also contains a small amount of dibutylamine with a concentration of about 1.25%. Upon calculation, the conversion rate of dibutylamine is up to more than 98%, and its selectivity is up to 99%.

Flash dewatering and vacuum rectification are performed to the above reaction product, and the purified and refined product is subjected to chromatographic analysis, the concentration of which is measure to be about 99.21%, and the index of refraction $N_D$ (20) of which is measured to be 1.440, suggesting that after purification and refining, N,N-dibutyl formamide with a purity of higher than 99% is obtained, which reaches a reagent grade.

Embodiment 5: Preparation of N,N-Diisopropyl Formamide 255.7 g of methanoic acid with a purity of 85% (i.e., containing water 38.3 g) and 460 g of diisopropylamine with a purity of 99% are added into a high-pressure reactor with a volume of 1 litre, a stirrer is started, and the mixture is stirred uniformly, so as to obtain a homogeneous reaction system, wherein molar ratio of methanoic acid to diisopropylamine is 1.05:1.

With stirring continuing, the above homogeneous reaction system is heated to 200° C. The pressure in the high-pressure reactor rises to about 1.7 MPa and no higher, the reaction is maintained for about 3 hours, then carbon monoxide and steam in the high-pressure reactor are vented, and the reaction product is collected, so as to obtain about 709 g of a homogeneous transparent solution.

Upon chromatographic analysis and comparison of the above reaction product, it is determined that N,N-diisopropyl formamide with a concentration of about 72.23% is obtained, the product also contains diisopropylamine with a concentration of about 27.38%. Upon calculation, the conversion rate of diisopropylamine is up to more than 72%, and its selectivity is 99%.

Flash dewatering and vacuum rectification are adopted to perform purification and refining to the above reaction product, so as to recycle diisopropylamine therein, and the purified and refined product is subjected to chromatographic analysis, the purity of which is measure to be about 99.96%, and the index of refraction $N_D$ (20) of which is measure to be 1.4370, suggesting that after purification and refining, N,N-diisopropyl formamide with a purity of higher than 99% is obtained, reaching a reagent grade.

Embodiment 6: Preparation of N,N-Diisobutyl Formamide 227.3 g of methanoic acid with a purity of 85% (i.e., containing water 34.1 g) and 522.2 g of diisobutylamine with a purity of 99% are added into a high-pressure reactor of 1 litre, a stirrer is started to mix the above substances homogeneously, so as to obtain a homogeneous reaction system, wherein molar ratio of methanoic acid to diisobutylamine is 1.05:1.

With stirring continuing, the above homogeneous reaction system is heated to 160° C. and kept at the temperature for about 40 minutes, and is then heated to about 200° C. The pressure in the high-pressure reactor rises to about 1.7 MPa and no higher, the reaction is maintained for about 3 hours, then carbon monoxide and steam in the high-pressure reactor are vented, and the reaction product is collected, so as to obtain about 743 g of a homogeneous transparent solution.

The above reaction product is subjected to chromatographic analysis and comparison, the obtained chromatographic analysis result is compared with that of a standard sample, so as to determine that the obtained product contains N,N-diisobutyl formamide with a concentration of about 99.58%, the product also contains a small amount of diisobutylamine with a concentration of about 0.34%. Upon calculation, the conversion rate of diisobutylamine is up to more than 99%, and the generated N,N-diisobutyl formamide has a selectivity of 99%.

The above reaction product is subjected to flash separation, and the purified and refined product undergoes chromatographic analysis, the index of refraction $N_D$ (20) of which is measure to be 1.4416, and the purity of which reaches a reagent grade.

Embodiment 7: Preparation of N-n-Butyl Formamide (Butyl Formamide)

272.7 g of methanoic acid with a purity of 85% (i.e., containing water 40.9 g) and 351 g of n-butylamine with a purity of 99% are added into a high-pressure reactor with a volume of 1 litre, and the mixture is stirred to obtain a homogeneous reaction system, wherein molar ratio of methanoic acid to n-butylamine is 1.05:1.

With stirring continuing, the above homogeneous reaction system is heated to 190° C. The pressure in the high-pressure reactor rises to about 1.3 MPa and no higher, the reaction is maintained for about 2.5 hours, then carbon monoxide and steam in the high-pressure reactor are vented, and the reaction product is collected, so as to obtain about 615 g of a homogeneous transparent solution.

The above reaction product is subjected to chromatographic analysis and comparison, so as to determine that N-n-butyl formamide with a concentration of about 99.20% is obtained, the product also contains a small amount of n-butylamine with a concentration of about 0.15%. Upon calculation, the conversion rate of n-butylamine is up to more than 99%, and its selectivity is up to more than 99%.

The above N-n-butyl formamide already has a purity of up to a reagent grade, and can hence be directly applied after flash dewatering, or may be further purified and refined according to practical needs, thereby obtaining N-n-butyl formamide with a higher purity.

Embodiment 8: Preparation of N,N-Dioctyl Formamide

Figure 3:
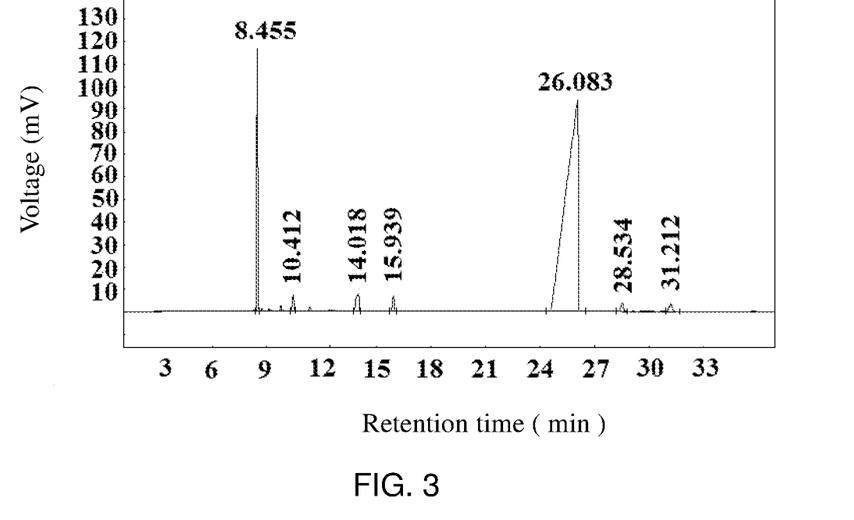
FIG. 3 is a chromatogram for the raw material of dioctyl amine in embodiment 8.

To enhance the credibility of product detection and analysis conclusions, the raw material is also subjected to chromatographic analysis. Gas chromatography test results of the used raw material of dioctyl amine are shown in Table 3, with a chromatogram referred to FIG. 3 (using a gas chromatography column with a length of 60 meters, under the following specific test conditions: pressure before the column: 0.1 MPa, air pressure: 0.03 MPa, pressure of hydrogen gas: 0.025 MPa, temperature in the column box: 155 □, evaporation temperature: 220° C., detection temperature: 220° C., measurement range: 9, sample injection fashion: split injection, split flow rate: 21.7 mL/min, injection volume: 1 μL). It can be seen from the chromatographic test result that, the appearance time of dioctyl amine is about 10 minutes, the purity of the raw material of dioctyl amine is about 96.1%, and the raw material of dioctyl amine contains a small amount of impurities.

31.4 g of methanoic acid with a purity of 98% (i.e., containing water 0.628 g) and 50 g of dioxane solvent are added into a high-pressure reactor with a volume of 1 litre, a stirrer is started and 157 g of dioctyl amine is added via a constant-flux pump into the high-pressure reactor, and the mixture is stirred uniformly, so as to obtain a homogeneous reaction system, wherein molar ratio of methanoic acid to dioctyl amine is 1.08:1.

With stirring continuing, the above homogeneous reaction system is heated to 160° C. and kept at the temperature for about 30 minutes, and is then heated to about 190° C. The pressure in the high-pressure reactor rises to about 1.5 MPa and no higher, the reaction is maintained for about 2.5 hours, then carbon monoxide and steam in the high-pressure reactor are vented, and the reaction product is collected, so as to obtain about 236.9 g of a homogeneous transparent light brown solution.

Figure 4:
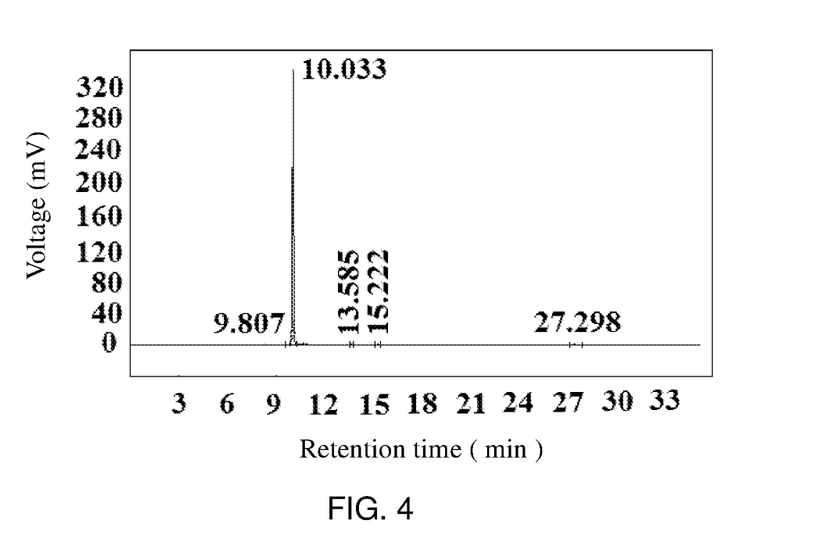
FIG. 4 is a chromatogram for the reaction product in embodiment 8.

Gas chromatographic analysis results of the above reaction product are shown in Table 4, with an obtained chromatogram referred to FIG. 4. According to Table 4 and FIG. 4, several chromatographic peaks are present. Upon comparison with the retention time of a standard sample, and in combination with the gas chromatographic analysis result of the above raw material of dioctyl amine, it can be determined that the reaction product contains N,N-dioctyl formamide with a concentration of about 87.46%, and also contains a small amount of incompletely reacted dioctyl amine with a concentration of about 0.74%, as well as solvent dioxane with a concentration of about 7.75%, and the remaining chromatographic peaks represent impurities introduced by the raw material of dioctyl amine and by products generated during the reaction process.

Upon calculation, in this embodiment, the conversion rate of dioctyl amine is up to more than 98%, and its selectivity is up to more than 99%.

TABLE 3

| Number | Retention time (minute) | Name | Concentration (%) | Chromatographic peak area |
|---|---|---|---|---|
| 1 | 9.807 |  | 0.8978 | 14171 |
| 2 | 10.033 | Dioctyl amine | 96.1 | 1516874 |
| 3 | 13.585 | Raw material impurity | 0.6888 | 10872 |
| 4 | 15.222 | Raw material impurity | 0.83 | 13101 |
| 5 | 27.298 |  | 1.48 | 23351 |
| sum |  |  | 100 | 1578369 |

TABLE 4

| Number | Retention time (minute) | Name | Concentration (%) | Chromatographic peak area |
|---|---|---|---|---|
| 1 | 8.4550 | Dioxane | 7.7500 | 376823 |
| 2 | 10.412 | Dioctyl amine | 0.7455 | 36241 |
| 3 | 14.018 | Raw material impurity | 1.6789 | 81613 |
| 4 | 15.939 | Raw material impurity | 0.8357 | 40623 |
| 5 | 26.083 | N,N-dioctyl formamide | 87.460 | 4251490 |
| 6 | 28.534 | By product | 0.7808 | 37957 |
| 7 | 31.212 | By product | 0.7500 | 36460 |
| Sum |  |  | 100 | 4861207 |

Embodiment 9: Preparation of N-Cyclohexyl Formamide 255.7 g of methanoic acid with purity of 85% (i.e., containing water 38.4 g) and 446.3 g of cyclohexylamine with a purity of 99% are added into a high-pressure reactor with a volume of 1 litre, the mixture are mixed uniformly, so as to obtain a homogeneous reaction system, wherein molar ratio of methanoic acid to cyclohexylamine is 1.06:1.

With stirring continuing, the above homogeneous reaction system is heated to about 190° C. The pressure in the high-pressure reactor rises to about 1.3 MPa and no higher, the reaction is maintained for about 2.5 hours, then carbon monoxide and steam in the high-pressure reactor are vented, and the reaction product is collected, so as to obtain about 694 g of a homogeneous transparent solution.

The above reaction product is subjected to chromatographic analysis, and the obtained chromatographic analysis result is compared with that of a standard sample, so as to determine the obtained product contains N-cyclohexyl formamide with a concentration of about 99.84%, the product also contains an extremely small amount of incompletely reacted cyclohexylamine with a concentration of about 0.10%. Upon calculation, the conversion rate of cyclohexylamine is up to more than 99%, and the generated N-cyclohexyl formamide has a selectivity of up to more than 99%.

The above reaction product is subjected to vacuum rectification, so as to obtain N-cyclohexyl formamide product with a purity of greater than 99%, reaching a reagent grade.

Embodiment 10: Preparation of N-Phenyl Formamide 103.2 g of methanoic acid with purity of 98% (i.e., containing water 2.06 g) is added into a high-pressure reactor with a volume of 1 litre, a stirrer is started and 190.1 g of aniline with a purity of 98% is added via a constant-flux pump into the high-pressure reactor, and the mixture is stirred uniformly, so as to obtain a homogeneous reaction system, wherein molar ratio of methanoic acid to aniline is 1.1:1.

With stirring continuing, the above homogeneous reaction system is heated to about 190° C. The pressure in the high-pressure reactor rises to about 1.5 MPa and no higher, the reaction is maintained for about 1.5 hours, then carbon monoxide and steam in the high-pressure reactor are vented, and the reaction product is collected, so as to obtain about 290.3 g of a homogeneous transparent solution.

The above reaction product is subjected to chromatographic analysis, and the obtained chromatographic analysis result is compared with that of a standard sample, so as to determine that the obtained product contains N-phenyl formamide with a concentration of 84.78%, and the reaction product also contains a small amount of incompletely reacted aniline with a concentration of about 12.35%. Upon calculation, the conversion rate of aniline is 87.6%, and the generated N-phenyl formamide has a selectivity of 97.5%.

Embodiment 11: Preparation of N-Hydroxyethyl Formamide 227.3 g of methanoic acid with purity of 85% (i.e., containing water 34.095 g) is added into a high-pressure reactor with a volume of 1 litre, a stirrer is started and 241.9 g of monoethanolamine (ethanolamine) with a purity of 99% is added via a constant-flux pump into the high-pressure reactor, and the mixture is stirred uniformly, so as to obtain a homogeneous reaction system, wherein molar ratio of methanoic acid to ethanolamine is 1.07:1.

With stirring continuing, the above homogeneous reaction system is heated to about 190° C. The pressure in the high-pressure reactor rises to about 1.3 MPa and no higher, the reaction is maintained for about 2.5 hours, then carbon monoxide and steam in the high-pressure reactor are vented, and the reaction product is collected, so as to obtain about 460 g of a homogeneous transparent solution.

The above reaction product is subjected to chromatographic analysis, and the obtained chromatographic analysis result is compared with that of a standard sample, so as to determine that the obtained product contains N-hydroxyethyl formamide with a concentration of about 97.04%, the reaction product also contains a small amount of incompletely reacted monoethanolamine with a concentration of about 0.57%. Upon calculation, the conversion rate of monoethanolamine is up to more than 99%; and the generated N-hydroxyethyl formamide has a selectivity of 98%.

Embodiment 12: Preparation of N-Formyl Morpholine 297.6 g of methanoic acid with purity of 85% (i.e., containing water 44.6 g) and 440 g of morpholine with a purity of 98% are added into a high-pressure reactor with a volume of 1 litre, and the mixture is stirred uniformly, so as to obtain a homogeneous reaction system, wherein molar ratio of methanoic acid to morpholine is 1.1:1.

With stirring continuing, the above homogeneous reaction system is heated to 190° C. The pressure in the high-pressure reactor rises to about 1.3 MPa and no higher, the reaction is maintained for about 2.5 hours, then carbon monoxide and steam in the high-pressure reactor are vented, and the reaction product is collected, so as to obtain about 722 g of homogeneous transparent solution.

The above reaction product is subjected to chromatographic analysis, and the obtained chromatographic analysis result is compared with that of a standard sample, so as to determine that the obtained product contains N-formyl morpholine with a concentration of about 97.20%, the product also contains a small amount of incompletely reacted morpholine with a concentration of about 0.50%. Upon calculation, the conversion rate of morpholine raw material is up to more than 99%, and its selectivity is up to 98%.

Flash dewatering and vacuum rectification are performed to the above reaction product, and the purified and refined product is subjected to chromatographic analysis, the concentration of which is measure to be about 99.88%, and the index of refraction $N_D$ (20) of which is measured to be 1.4850, suggesting that after purification and refining, N-formyl morpholine with a purity of higher than a reagent grade is obtained.

Embodiment 13: Preparation of 4-Methylbenzamide (p-Toluamide)

51.6 g of methanoic acid with purity of 98% (i.e., containing water 1.03 g) and 50 g of solvent dimethylformamide are added into a high-pressure reactor with a volume of 1 litre, a stirrer is started and 108 g of p-toluidine with a purity of 99% is added into the high-pressure reactor, and methanoic acid and p-toluidine at a molar ratio of 1.1:1 are mixed uniformly to obtain a homogeneous reaction system.

With stirring continuing, the above homogeneous reaction system is heated to 190° C. The pressure in the high-pressure reactor rises to about 1.8 MPa and no higher and is substantially kept stable, the reaction is maintained for about 2.5 hours, then carbon monoxide and steam in the high-pressure reactor are vented, and the reaction product is collected, so as to obtain about 205 g of homogeneous transparent solution.

The above reaction product is subjected to chromatographic analysis, and the obtained chromatographic analysis result is compared with the retention time of a standard sample, with the retention time of p-toluidine raw material and the solvent dimethylformamide taken into consideration, it is determined that, the obtained product contains 4-methylbenzamide with a concentration of about 47.86%, the product also contains a small amount of incompletely reacted p-toluidine with a concentration of about 35.57% as well as the solvent dimethylformamide with a concentration of about 13.18%. In addition, the reaction product also contains a small amount of by product with a concentration of about 1.62% generated during the reaction process. Upon calculation, the conversion rate of p-toluidine is about 58.2%, and its selectivity is up to 96.7%.

Embodiment 14: Preparation of N-Dodecyl Formamide 29.9 g of methanoic acid with a purity of 98% (i.e., containing water 0.6 g) and 90 g of solvent isopropanol are added into a high-pressure reactor with a volume of 1 litre, and 113.5 g of dodecylamine (laurylamine) with a purity of 98% are added during stirring, and the mixture are mixed uniformly to obtain a homogeneous reaction system, the molar ratio of methanoic acid to laurylamine is 1.05:1.

With stirring continuing, the above homogeneous reaction system is heated to 160° C. and kept at the temperature for about 35 minutes, and is then heated to about 190° C. The pressure in the high-pressure reactor rises to about 1.3 MPa and no higher, the reaction is maintained for about 2.5 hours, then carbon monoxide and steam in the high-pressure reactor are vented, and the reaction product is collected, so as to obtain about 231.4 g of homogeneous transparent solution.

The above reaction product is subjected to chromatographic analysis, and the obtained chromatographic analysis result is compared with that of a standard sample, so as to determine that the obtained product contains N-dodecyl formamide with a concentration of about 72.91%, the product also contains isopropanol solvent with a concentration of about 27.09%. Characteristic peaks of dodecylamine fail to be detected, therefore, dodecylamine can be determined as being converted almost completely, and both conversion rate and selectivity of dodecylamine reach more than 99%.

Embodiment 15: Preparation of N-Formyl Pyrrolidine 113.6 g of methanoic acid with a purity of 85% (i.e., containing water 17 g) is added into a high-pressure reactor with a volume of 1 litre, a stirrer is started and 143.7 g of pyrrolidine with a purity of 99% is added into the high-pressure reactor via a constant-flux pump, and the mixture are mixed uniformly to obtain a homogeneous reaction system, wherein the molar ratio of methanoic acid to pyrrolidine is 1.05:1.

With stirring continuing, the above homogeneous reaction system is heated to 190° C. The pressure in the high-pressure reactor rises to about 1.2 MPa and no higher, the reaction is maintained for about 2.5 hours, then carbon monoxide and steam in the high-pressure reactor are vented, and the reaction product is collected, so as to obtain about 254 g of homogeneous transparent solution.

The above reaction product is subjected to chromatographic analysis, and the obtained chromatographic analysis result is compared with that of a standard sample, so as to determine that the obtained product contains N-formyl pyrrolidine with a concentration of about 97.01%, the product also contains a small amount of incompletely reacted pyrrolidine with a concentration of about 2.99%. Upon calculation, the conversion rate of pyrrolidine is up to more than 97%, and its selectivity is 99%.

Experimental Example 16

113.6 g of methanoic acid with a purity of 85% (i.e., containing water 17.04 g) and 435.5 g of N,N-demethyldodecylamine with a purity of 98% are added into a high-pressure reactor with a volume of 1 litre, and are mixed uniformly to obtain a homogeneous liquid.

With stirring continuing, the above homogeneous liquid is heated, first to about 160° C. and kept at the temperature for about 35 minutes, and is then heated to about 190° C., the reaction is maintained for about 2.5 hours. The pressure in the high-pressure reactor rises to about 3.45 MPa and changes no more, then carbon monoxide and steam in the high-pressure reactor are vented, and the reaction product is collected, so as to obtain about 489 g of a homogeneous transparent solution.

Figure 5:
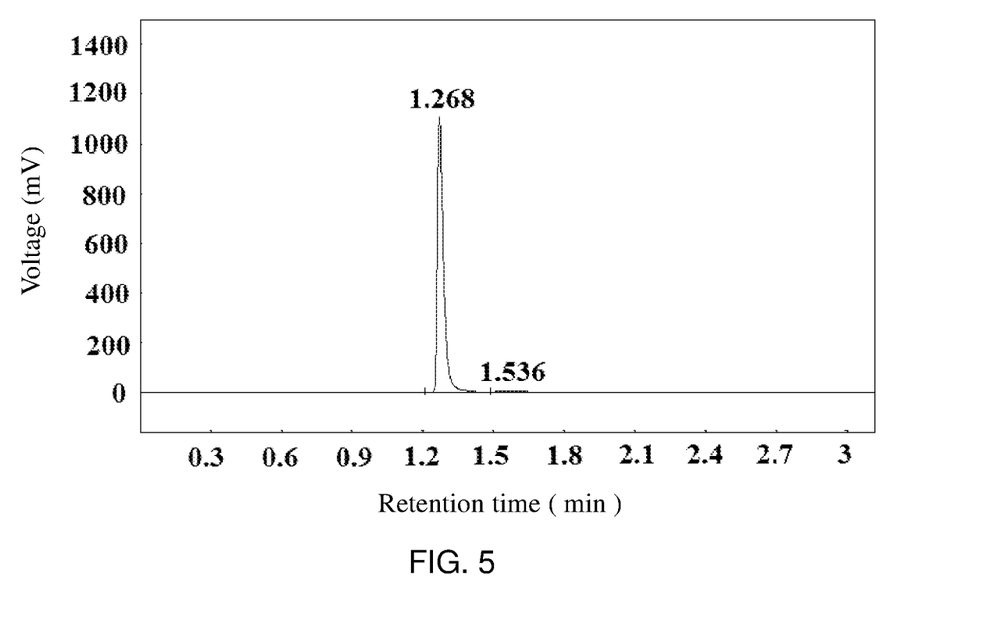
FIG. 5 is a chromatogram for the reaction raw material of N,N-demethyldodecylamine in experimental example 1.
Figure 6:
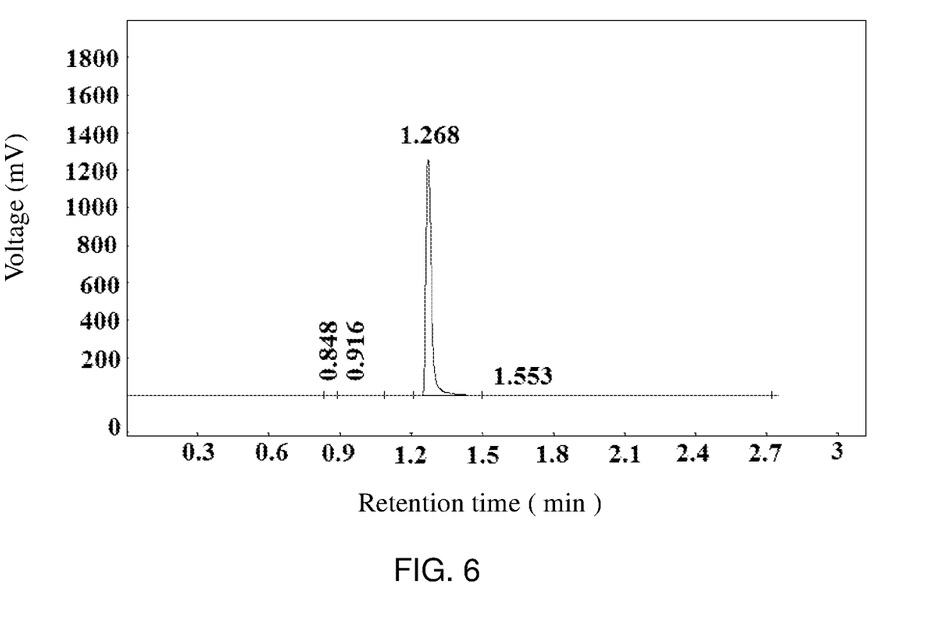
FIG. 6 is a chromatogram for the reaction product in experimental example 1.

Chromatographic analysis result of the above raw material of N,N-demethyldodecylamine is referred to Table 5 and FIG. 5 (using a gas chromatography column with a length of 30 meters, an inner diameter of 0.53 mm, a film thickness of 0.5 µm, and an immobile liquid of AE.PEG-20M. The analysis is carried out under the following specific test conditions: pressure before the column: 0.03 MPa, air pressure: 0.03 MPa, pressure of hydrogen gas: 0.025 MPa, temperature in the column box: 280° C., evaporation temperature: 300° C., test temperature: 300° C., measuring range: 9, sample injection fashion: split injection, split flow rate: 75 mL/min, and sample injection volume: 0.2 µL). According to the chromatographic analysis result, the retention time of N,N-demethyldodecylamine can be determined as 1.268 minute, and the concentration about 98.25%. The chromatographic analysis result of the reaction product is referred to Table 6 and FIG. 6, and is compared with the chromatographic analysis result of the raw material of N,N-demethyldodecylamine, and the chromatogram of the reaction product is basically consistent with that of the raw material, the retention time corresponding to the chromatographic peak is also 1.268 minute, and the concentration is about 99.44%, therefore, it can be determined that, the main component of the reaction product is N,N-demethyldodecylamine, suggesting that no expected reactions occur in the homogeneous system formed between the raw material of N,N-demethyldodecylamine and methanoic acid.

TABLE 5

| Number | Retention time (minute) | Name | Concentration (%) | Chromatographic peak area |
|---|---|---|---|---|
| 1 | 1.268 | N,N-demethyldodecylamine | 98.25 | 1990626 |
| 2 | 37.826 | | 1.746 | 35368 |
| sum | | | 100 | 2025994 |

TABLE 6

| Number | Retention time (minute) | Name | Concentration (%) | Chromatographic peak area |
|---|---|---|---|---|
| 1 | 0.844 | | 0.005865 | 120 |
| 2 | 0.916 | | 0.01238 | 254 |
| 3 | 1.268 | N,N-demethyldodecylamine | 99.44 | 2036804 |
| 4 | 1.553 | | 0.5431 | 11124 |
| Sum | | | 100 | 2048302 |

According to the above embodiments, it is further understandable that, adopting the preparation method of the present application, with methanoic acid and a primary amine or a secondary amine compound as the reaction raw materials to undergo a homogeneous reaction, and without using a catalyst, can obtain a formamide compound. The preparation method has few by-reactions, the primary amine or the secondary amine compound has a very high selectivity, and the preparation technique is simple and controllable in operation. Even if part of the raw material of the primary amine or the secondary amine compound has a slightly low conversion rate (compared with that in other embodiments of the present application), unreacted raw materials can be readily recycled and reused through purification and refining of the reaction product. At the same time, a formamide product with a reagent grade can be obtained from the reaction product upon simple purification and refining.

Finally, it should be noted that, the above embodiments are merely meant to illustrate rather than limit the technical solutions of the present application; and although the present application has been concretely described in reference to the above embodiments, one with ordinary skill in the art shall understand that modifications can still be made to the technical solutions recorded in the foregoing embodiments, or that equivalent substitutions can still be made to part or all of the technical features therein; neither these modifications nor these substitutions shall make the essence of the corresponding technical solutions depart from the scope of the technical solutions in the above embodiments of the present application.

What is claimed is:

1. A preparation method of formamide compound, consisting of steps of:
   mixing raw materials of methanoic acid and an amine compound selected from a primary amine or a secondary amine to prepare a homogeneous reaction system;
   heating the homogeneous reaction system in a high-pressure reactor to 160° C. or higher, keeping temperature for a period of time, then continuing to heat the homogeneous reaction system to react until a pressure in the high-pressure reactor rises to 1.0-3.0 MPa and no higher, keeping reaction for 1-5 hours, and collecting reaction product to obtain the formamide compound.

2. The preparation method according to claim 1, wherein the homogeneous reaction system contains a solvent, which is water or a solvent miscible with water, or a solvent immiscible with water but miscible with the generated formamide compound.

3. The preparation method according to claim 2, wherein the solvent is water formed during preparing the homogeneous reaction system from methanoic acid and the amine compound, and/or water added during preparing the homogeneous reaction system from methanoic acid and the amine compound, and/or an organic solvent selected from one or more of dioxane, tetrahydrofuran, methanol, ethanol, isopropanol, dimethylformamide, toluene and xylene.

4. The preparation method according to claim 1, wherein, when preparing the homogeneous reaction system, molar ratio of methanoic acid to the primary amine compound or the secondary amine compound is 1.0-1.3.

5. The preparation method according to claim 2, wherein, when preparing the homogeneous reaction system, molar ratio of methanoic acid to the primary amine compound or the secondary amine compound is 1.0-1.3.

6. The preparation method according to claim 3, wherein, when preparing the homogeneous reaction system, molar ratio of methanoic acid to the primary amine compound or the secondary amine compound is 1.0-1.3.

7. The preparation method according to claim 1, wherein,
the amine compound of the primary amine or the secondary amine has a molecular formula R1R2NH, in which R1 and R2 are independently selected from hydrogen but not both hydrogen, $C_1$-$C_{14}$ hydrocarbyl group, and $C_1$-$C_{14}$ hydrocarbyl group containing 1-2 substituent groups; or,
the primary amine or the secondary amine compound is a five-membered nitrogen-containing heterocyclic ring or a six-membered nitrogen-containing heterocyclic ring compound with at least one active hydrogen in the molecule, and the five-membered nitrogen-containing heterocyclic ring or the six-membered nitrogen-containing heterocyclic ring does not contain substituent group or contains 1-2 substituent groups;
the 1-2 substituent groups are selected from halogen, nitro group, cyano group, lower alkoxy group, hydroxyl group or secondary amino group of a lower alkyl.

8. The preparation method according to claim 7, wherein,
the amine compound of the primary amine or the secondary amine has a molecular formula R1R2NH, in which R1 is hydrogen, $C_1$-$C_{14}$ hydrocarbyl group or $C_1$-$C_{14}$ hydrocarbyl group containing 1-2 substituent groups; and R2 is C2-C14 hydrocarbyl group or $C_2$-$C_{14}$ hydrocarbyl group containing 1-2 substituent groups;
or,
the primary amine or the secondary amine compound is a five-membered nitrogen-containing heterocyclic ring or a six-membered nitrogen-containing heterocyclic ring compound with a pyrrolyl, a pyrrolidyl, a imidazolyl, a morpholino or a piperazinyl group.

9. The preparation method according to claim 7, wherein, the hydrocarbyl group is selected from alkane group, cycloalkyl group or aryl group.

10. The preparation method according to claim 8, wherein, the hydrocarbyl group is selected from alkane group, cycloalkyl group or aryl group.

11. The preparation method according to claim 1, wherein, the amine compound of the primary amine or the secondary amine is selected from diethylamine, dipropylamine, diisopropylamine, dibutylamine, diisobutylamine or n-butylamine.

12. The preparation method according to claim 7, wherein, the amine compound of the primary amine or the secondary amine is selected from diethylamine, dipropylamine, diisopropylamine, dibutylamine, diisobutylamine or n-butylamine.

13. The preparation method according to claim 1, further comprising performing purification and refining to the reaction product.

14. The preparation method according to claim 2, further comprising performing purification and refining to the reaction product.

15. The preparation method according to claim 3, further comprising performing purification and refining to the reaction product.

16. The preparation method according to claim 4, further comprising performing purification and refining to the reaction product.

17. The preparation method according to claim 7, further comprising performing purification and refining to the reaction product.

18. The preparation method according to claim 1, wherein the temperature is kept for 30-55 minutes.

19. The preparation method according to claim 1, wherein heating the homogeneous reaction system in the high-pressure reactor to 160° C. or higher, keeping temperature for 30-55 minutes, then continuing to heat the homogeneous reaction system to 190-230° C. to react until the pressure in the high-pressure reactor rises to 1.0-3.0 MPa and no higher.

* * * * *